US008546338B2

(12) United States Patent
Donners et al.

(10) Patent No.: US 8,546,338 B2
(45) Date of Patent: Oct. 1, 2013

(54) SELF-ASSEMBLING HYDROGELS BASED ON DICEPHALIC PEPTIDE AMPHIPHILES

(75) Inventors: Jackie J. Donners, West Windsor, NJ (US); Aruna Nathan, Bridgewater, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 265 days.

(21) Appl. No.: 12/962,775

(22) Filed: Dec. 8, 2010

(65) Prior Publication Data

US 2012/0148674 A1 Jun. 14, 2012

(51) Int. Cl.
*A61K 38/08* (2006.01)
*A61K 38/03* (2006.01)

(52) U.S. Cl.
USPC .......................................... 514/21.6; 530/323

(58) Field of Classification Search
None
See application file for complete search history.

(56) References Cited

U.S. PATENT DOCUMENTS

| | | | |
|---|---|---|---|
| 6,693,167 | B1 | 2/2004 | Camilleri |
| 6,890,654 | B2 | 5/2005 | Stupp |
| 7,425,645 | B2 | 9/2008 | Castro |
| 7,510,873 | B2 | 3/2009 | Mistry et al. |
| 2002/0132974 | A1 | 9/2002 | Boden |
| 2002/0160471 | A1 | 10/2002 | Kisiday |
| 2004/0242469 | A1 | 12/2004 | Lee |
| 2005/0181973 | A1 | 8/2005 | Genove |
| 2005/0208589 | A1 | 9/2005 | Stupp |
| 2005/0209145 | A1 | 9/2005 | Stupp |
| 2005/0272662 | A1 | 12/2005 | Stupp |
| 2005/0287186 | A1 | 12/2005 | Ellis Behnke |
| 2006/0019309 | A1 | 1/2006 | Zhang |
| 2006/0110437 | A1 | 5/2006 | Stupp |
| 2006/0148734 | A1 | 7/2006 | Camilleri |
| 2006/0149036 | A1 | 7/2006 | Stupp |
| 2006/0154852 | A1 | 7/2006 | Boden |
| 2006/0241071 | A1 | 10/2006 | Grinstaff et al. |
| 2006/0247165 | A1 | 11/2006 | Stupp |
| 2007/0099840 | A1 | 5/2007 | Ulijn |
| 2007/0128175 | A1 | 6/2007 | Ozbas |
| 2007/0203062 | A1 | 8/2007 | Ellis Behnke |
| 2008/0112939 | A1 | 5/2008 | Colter |
| 2008/0199431 | A1 | 8/2008 | Capito |
| 2008/0299657 | A1 | 12/2008 | Stupp |
| 2009/0036851 | A1 | 2/2009 | Carlucci |
| 2009/0123553 | A1 | 5/2009 | Reches |
| 2009/0156427 | A1 | 6/2009 | Zhang |
| 2009/0238788 | A1 | 9/2009 | Butterick |
| 2009/0263429 | A1 | 10/2009 | Ulijn |
| 2010/0010560 | A1 | 1/2010 | Taylor |
| 2010/0034881 | A1 | 2/2010 | Schneider |
| 2010/0040880 | A1 | 2/2010 | Koopmans |
| 2011/0076769 | A1 | 3/2011 | Colter et al. |

FOREIGN PATENT DOCUMENTS

| | | |
|---|---|---|
| EP | 1523494 B1 | 12/2009 |
| WO | WO 99/29712 A1 | 6/1999 |
| WO | WO 0230957 A1 | 4/2002 |
| WO | WO 0250100 A2 | 6/2002 |
| WO | WO 03054146 A2 | 7/2003 |
| WO | WO 03070749 A2 | 8/2003 |
| WO | WO 03084980 A2 | 10/2003 |
| WO | WO 2004003561 A1 | 1/2004 |
| WO | WO 2004007683 A2 | 1/2004 |
| WO | WO 2004018628 A2 | 3/2004 |
| WO | WO 2006076042 A2 | 7/2006 |
| WO | WO 2007027725 A2 | 3/2007 |
| WO | WO 2007043048 A2 | 4/2007 |
| WO | WO 2008061014 A2 | 5/2008 |
| WO | WO 2008063808 A2 | 5/2008 |
| WO | WO 2008067145 A2 | 6/2008 |
| WO | WO 2008113030 A2 | 9/2008 |
| WO | WO 2008131052 A2 | 10/2008 |
| WO | WO 2008134544 A1 | 11/2008 |
| WO | WO 2009026233 A2 | 2/2009 |

OTHER PUBLICATIONS

Marullo et al 'Controlling Self-assembly properties of peptide amphiphiles' retrieved from http://www.chemengr.ucsb.edu/~ceweb/gss/pdfs/marullo.pdf on Jan. 17, 2013, 1 page.*
Lin et al 'Employing Thiol-Ene radical and azide-acetylene click chemistries for the preparation of new polycephalic peptide amphiphiles; from synethesis to applications' 2009 AICHE meeting, retrieved from http://www3.aiche.org/Proceedings/Abstract.aspx?PaperID=162586 on Jan. 17, 2013, 3 pages.*
Colombo et al 'Peptide self-assembly at the nanoscale: a challenging target for computational and experimental biotechnology' Trends in biotechnology v25(5) 2007 pp. 211-218.*
Smialowski et al 'Protein solubility:sequence based prediction and experimental verification' Bioinformatics v23(19) 2007 pp. 2536-2542.*
Niiranen et al 'Comparative expression study to increase the solubility of cold adapted *Vibrio* proteins in *Escherichia coli*' Protein Expression and Purification v52 2007 pp. 210-218.*
Harrington et al 'Branched peptide-amphiphiles as self-assembling coatings for tissue engineering scaffolds' Journal of Biomedical Materials Research Part A 2006 pp. 157-167.*
N.A.J.M. Sommerdijk et al., Dicephalic Surfactants, *Chem. Commun.*, 1998, 743-744.
R. Skrzela et al., Expirimental and Theoretical Approach to Nonequivalent Adsorption of Novel Dicephalic Ammonium Surfactants at the Air/Solution Interface, *J. Phys. Chem.*, 2010, 114, 10471-10480.
K.A. Wilk et al., Structural Aspects in Saccharide-Derived Micelles Studied by a Spin Probe Technique, Colloids and Surfaces A: Physiocochem. Eng. Aspects, 343, 64-69, 2009.
Tony Le Gall et al., Synthesis and Transfection Properties of a Series of Lipidic Neamine Derivatives, Bioconjugate Chemistry, vol. 20, No. 11, Nov. 18, 2009, pp. 2032-2046.
PCT International Search Report for Application No. PCT/US2011/063747, dated Mar. 7, 2012.

* cited by examiner

*Primary Examiner* — Cecilia J Tsang
*Assistant Examiner* — Ronald Niebauer

(57) ABSTRACT

We have disclosed dicephalic amphiphiles having peptide sequences as the head groups. We have also disclosed self-assembly hydrogels prepared from the dicephalic peptide amphiphiles. These hydrogels are useful for the encapsulation and delivery of bioactives to a patient.

4 Claims, 13 Drawing Sheets

8 acid groups/
molecule

SEQUENCE LISTING

```
<160> NUMBER OF SEQ ID NOS: 43

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Ala Val Ala Val Ala Lys Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Gly Phe Gly Phe Gly Lys Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Ala Val Ala Val Ala Glu Glu Glu
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Gly Val Ala Val Ala Val Ala Glu Gly Glu
1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Gly Phe Gly Phe Gly Glu Gly Glu
1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Gly Phe Gly Phe Gly Phe Gly Glu Gly Glu
1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Trp Gly Trp Gly Trp Gly Glu Gly Glu
1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Phe Gly Phe Gly Phe Gly Gln Gln Ser
1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Trp Gly Trp Gly Trp Gly Gln Gln Ser
1               5                  10

<210> SEQ ID NO 10
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Gly Tyr Gly Tyr Gly Tyr Gly Gln Gln Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Gly Phe Gly Phe Gly Asn Asn Ser
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Gly Phe Gly Phe Gly Gln Gly Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Gly Phe Gly Phe Gly Gly Gln Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Phe Gly Phe Gly Phe Gly Asn Gly Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Gly Phe Gly Phe Gly Gly Asn Ser
1               5                   10
```

```
<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Phe Gly Phe Gly Phe Gly Glu Gly Ser
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Phe Gly Phe Gly Phe Gly Lys Gly Ser
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Ala Val Ala Val Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Val Ala Val Ala Val Ala
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Gly Phe Gly Phe Gly
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Gly Phe Gly Phe Gly Phe Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Phe Gly Phe Gly Phe Gly Glu Gly
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Trp Gly Trp Gly Trp Gly
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Tyr Gly Tyr Gly Tyr Gly
1               5

<210> SEQ ID NO 25
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Ala
1

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Glu Glu
1

<210> SEQ ID NO 27
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 27

Glu Gly Glu
1

<210> SEQ ID NO 28
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Gln Ser
1

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Asn Ser
1

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gly Ser
1

<210> SEQ ID NO 31
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gln Ser
1

<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Gly Ser
1
```

```
<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Asn Ser
1

<210> SEQ ID NO 34
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Gly Ser
1

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Gly Ser
1

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Phe Gly Phe Gly Phe Gly Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Gly Phe Gly Phe Gly Phe Gly
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

```
Gly Phe Gly Phe Gly Phe
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Ala Val Ala Val Ala Glu Gly Glu
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Phe Gly Phe Gly Phe Gly Gln Gly Gln
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Val Ala Val Ala Val Ala Glu Glu Glu
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Gly Phe Gly Phe Gly Glu Gly Glu
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Phe Gly Phe Gly Phe Gly Asn Gly Ser
1               5
```

SELF-ASSEMBLING HYDROGELS BASED ON DICEPHALIC PEPTIDE AMPHIPHILES

SEQUENCE LISTING

The instant application contains a Sequence Listing which has been submitted in ASCII format via EFS-Web and is hereby incorporated by reference in its entirety. Said ASCII copy, created on Feb. 23, 2011, is named RTX5024U.txt and is 9,446 bytes in size.

FIELD OF THE INVENTION

The invention relates to dicephalic peptide amphiphiles. The invention further relates to self-assembled hydrogels prepared from dicephalic peptide amphiphiles.

BACKGROUND OF THE INVENTION

Therapeutic delivery of proteins and cells, such as stem cells is currently accomplished by either systemic administration or bolus injection at the injury site. In both cases, only a relatively small percentage of active remains at the injury site and the bulk of the active end up in other organs like the liver and the lungs. An approach in which the actives are retained at the injury site would allow for lower dosage, less side effects and potentially higher activity.

Current approaches for cell and protein delivery include microspheres, physisorption to matrices like foams and covalent attachment to such matrices. Often these approaches are compatible with delivery through small gauge needles required for delicate tissues like the brain and heart. Hydrogels have the benefit that they are deformable and in some cases can be formed in situ. However, the predominant mechanisms of hydrogel formation are through photo-crosslinking or radical cross-linking, both of which cause harm to proteins and cells. A few approaches have been reported that are cell and protein compatible. Enzymatically cross-linked gels and gels formed by cross-linking through Michael addition have been reported, however the rate of formation is such that these gels need to be pre-formed ex situ and then introduced in situ.

Self-assembling peptide systems have the benefit that when designed properly, they can be in a liquid state ex situ and rapidly transform into a gel state when in contact with body fluid in situ. Since the gelation mechanism is based on non-covalent interactions, no harm to proteins and cells is expected. A system based on peptides with alternating hydrophobic and charged residues has been reported that self-assemble due to beta sheet type hydrogen-bonding interactions between the peptides. The potential drawback of these systems is that it relies on a delicate balance in charge which limits the scope of accessible sequences. Hydrogels based on Fmoc-protected diphenylalanine are prepared by injecting a solution of the peptide in hexafluoroisopropanol, an undesirable solvent and there may also be concerns about the toxicity of the Fmoc protecting group upon degradation of the peptide. A variant was reported in which Fmoc-protected phenylalanine is coupled to phenylalanine by an enzyme. Potential drawbacks are potential immune response to the enzyme and a slower reaction rate. Systems based on beta hairpin peptides have been reported that are introduced by shear-thinning through a cannula after which they re-form. Finally hydrogels based on beta-sheet forming peptide sequences and hydrogels based on coiled coils of alpha-helical peptides have been reported as well. Finally, there is an extensive body of work from around linear peptide amphiphiles which are peptides that on either the C- or N-terminus are functionalized with an alkyl tail. The advantage of these systems is that the additional energy gain of the hydrophobic collapse of the tails stabilizes the system. Linear molecules (single head, single $C_6$-$C_{22}$ tail) of which the peptide head group can be branched and bola-amphiphiles (head-tail-head arrangement) are described. A drawback of this system is that in general supraphysiological concentrations of divalent ions or substantial pH change is required to induce gelation. In addition, these gels do not display shear-thin behavior.

There are four major classes of amphiphiles: linear amphiphiles (single head, single tail), bola-amphiphiles (head-tail-head), gemini amphiphiles (two head groups, two tails) and dicephalic amphiphiles (two head groups, one tail). It has been shown that these classes exhibit different aggregation behavior compared to one another. An advantage of gemini and dicephalic amphiphiles is that they are 'pre-polymerized' and therefore form stable aggregates at lower critical aggregation concentrations. Gemini amphiphiles based on multiple positively charged peptides have been reported for use as gene transfection agents. Three dicephalic amphiphile systems are described hereafter. The first reported system comprises an amphiphile with a diphosphate head group that forms rectangular micellar aggregates. The two other systems have ammonium or saccharide head groups and form micelles.

In light of the drawbacks of the hydrogels described above, there is still a need for alternative hydrogels for bioactive delivery. In particular, there is a need for in situ gelling self-assembly hydrogels that are easily delivered through a small gauge needle, gel upon delivery under physiological conditions, and do not have an adverse effect on the bioactive.

SUMMARY OF THE INVENTION

We describe herein dicephalic amphiphiles having peptide sequences as the head groups. These dicephalic peptide amphiphiles are useful in preparing self-assembly hydrogels. The peptide head groups induce gelation and increase solubility of the amphiphile in aqueous solutions, while the hydrophobic tail serves to stabilize the hydrogel. Furthermore, these hydrogels are useful for the encapsulation and delivery of bioactives to a patient.

DETAILED DESCRIPTION OF THE INVENTION

We describe herein dicephalic peptide amphiphiles (DPA) which form self-assembling hydrogels. The general structure of the dicephalic peptide amphiphile is shown below by the following Formula 1:

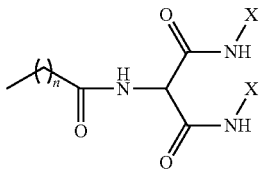

The length of the hydrocarbon chain designated by n is at least 6, and X is a peptide sequence, such as SEQ ID NO: 3, SEQ ID NO: 4, SEQ ID NO: 5, SEQ ID NO: 6, SEQ ID NO: 8, SEQ ID NO: 10, SEQ ID NO: 11, SEQ ID NO: 12, SEQ ID NO:13, SEQ ID NO: 14, SEQ ID NO: 15, SEQ ID NO: 16 and SEQ ID NO: 17, shown in Table 1. In one embodiment, n is the range of about 6 to about 22. In another embodiment, n is in the range of about 12 to about 18.

Figure 1:
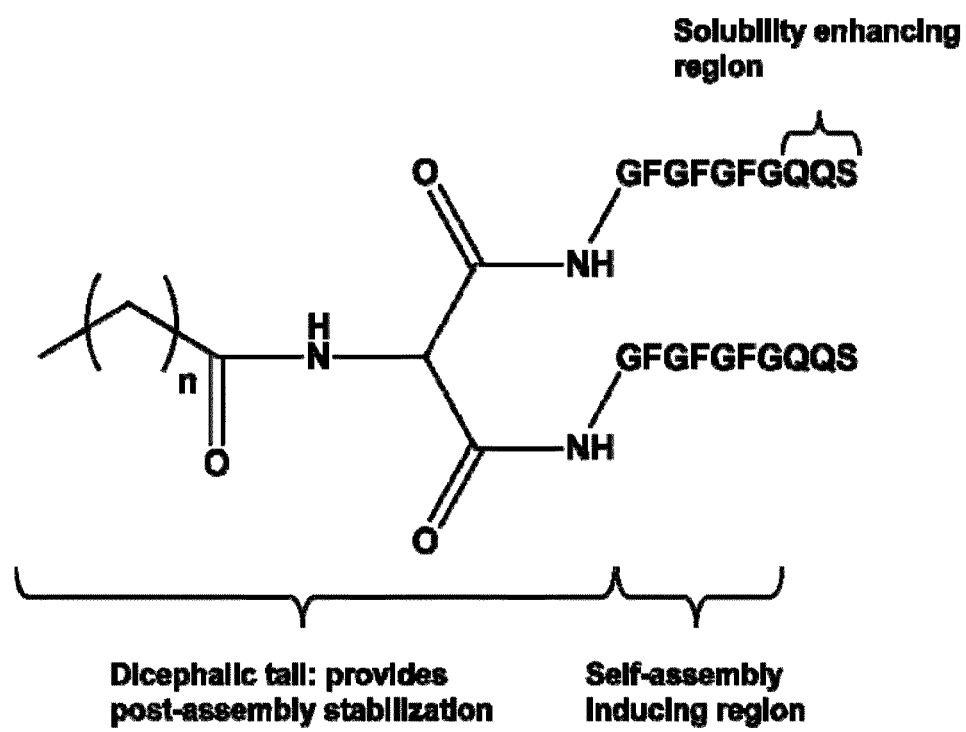
FIG. 1. Chemical drawing of an exemplary dicephalic peptide amphiphile, disclosing "GFGFGFGQQS" SEQ ID NO: 8.

The dicephalic peptide amphiphile has a hydrophobic tail and two peptide head groups. The hydrophobic tail provides stabilization to the hydrogel after self-assembly and the two head groups (X from Formula 1 above) have a peptide sequence. The peptide sequence has a self-assembly inducing region and a solubility enhancing region (FIG. 1), with the tail connecting to the N-terminus of the self-assembly inducing region. The self-assembly inducing region which provides directional secondary interactions to induce fiber formation and gelation has at least 4 amino acids. In one embodiment, the self-assembly inducing region has from about 6 to about 9 amino acids. In another embodiment, the self-assembly inducing region is a peptide sequence, such as SEQ ID NO: 18, SEQ ID NO: 19, SEQ ID NO: 20, SEQ ID NO: 21, SEQ ID NO: 22, and SEQ ID NO: 24.

The directional secondary interactions provided by the self-assembly inducing region include, but are not limited to beta-sheet type hydrogen bonding and pi-pi stacking interactions.

One example of a self-assembly inducing region having the beta-sheet type hydrogen bonding interactions is Val-Ala-Val-Ala-Val-Ala (SEQ ID NO: 18). Aromatic sequences that have the pi-pi stacking type interactions, include Gly-Phe-Gly-Phe-Gly-Phe-Gly (SEQ ID NO: 21), Gly-Phe-Gly-Phe-Gly-Phe-Gly-Phe-Gly (SEQ ID NO: 37), Gly-Tyr-Gly-Tyr-Gly-Tyr-Gly (SEQ ID NO: 24), Gly-Trp-Gly-Trp-Gly-Trp-Gly (SEQ ID NO: 23), and the like. The last sequence did not result in gels but large aggregates are formed. Both amphiphiles based on beta-sheet type hydrogen bonding interactions and pi-pi stacking interactions result in hydrogel formation, however, the hydrogels prepared from DPAs which were driven by pi-pi stacking interactions displayed rheological properties that were an order of magnitude larger than the hydrogels prepared from DPAs which were driven by beta-sheet hydrogen bonding interactions at the same concentration of amphiphile. In one embodiment the self-assembly inducing region provides pi-pi stacking interactions and has the peptide sequence Gly-Phe-Gly-Phe-Gly-Phe (SEQ ID NO:

The solubility enhancing region enables solubility of the dicephalic peptide amphiphile and plays a role in the kinetics of hydrogel formation. The solubility enhancing region has at least 1 amino acid, and in one embodiment, has at least 3 amino acids. In another embodiment, the solubility enhancing region has 3 amino acids. The solubility enhancing region has peptide sequences rich in polar residues that enhance solubility of the DPA in solution, for example in water, phosphate buffered saline, DMEM and the like. Suitable peptide sequences for the solubility enhancing region include, but are not limited to Glu-Gly-Glu (SEQ ID NO: 27), Glu-Glu-Glu (SEQ ID NO: 26), Gln-Gln-Ser (SEQ ID NO: 28), Asn-Asn-Ser (SEQ ID NO: 29), Gln-Gly-Ser (SEQ ID NO: 30), Gly-Gln-Ser (SEQ ID NO: 31), Asn-Gly-Ser (SEQ ID NO: 32), Gly-Asn-Ser (SEQ ID NO: 33), Glu-Gly-Ser (SEQ ID NO: 34) and Lys-Gly-Ser (SEQ ID NO: 35). A Lys-Ala (SEQ ID NO: 25) peptide sequence proved to be insoluble with the self-assembly inducing regions that were tested and therefore only peptide sequences with 3 or more polar amino acids were pursued. All Glu and Lys based permutations required supraphysiological divalent ion concentrations to induce gelation. However, all polar, non-charged amino acid based sequences (e.g. Asn, Gln and Ser based sequences) formed gels at physiological concentrations of divalent ions. In one embodiment, the solubility enhancing region is a peptide sequence, such as SEQ ID NO: 26 SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, and SEQ ID NO: 35.

It can be appreciated by those skilled in the art that the solubility enhancing region can be extended with peptide sequences displaying biological activity.

Dicephalic peptide amphiphiles were prepared in a three-step process. First the dicephalic tail was prepared by reacting fatty acid chloride (having a hydrocarbon chain length corresponding to n in Formula 1) with 2-amino-malonic acid dimethyl ester, followed by ester hydrolysis to generate the free acid. In the second step, the peptide sequence was prepared using solid state peptide synthesis technique, either manually or by automated synthesis. In the third step, the dicephalic tail was coupled to the peptide while still on the resin, using a tail:peptide mole ratio of 1:2. Interestingly, attempts to prepare a variant with only one peptide per tail failed, presumably because the dicephalic version is entropically favored. Finally, the dicephalic peptide amphiphile is cleaved from the resin and protecting groups on the peptide side chains are removed in a single step by treatment with trifluoroacetic acid (TFA). The molecules are then dissolved in water and lyophilized at pH 6-8 to remove residual acid.

The hydrogels resulting from the dicephalic peptide amphiphiles exhibit fluid-like properties ex situ whereas it will transform into a hydrogel encapsulating the bioactive in situ without denaturing or otherwise negatively affecting the activity of the bioactives. These hydrogels are useful for the therapeutic delivery of bioactives through small gauge cannulas. The gel will then retain the bioactives at the injury site such that the bioactives can exert their therapeutic action.

In one embodiment, hydrogels are prepared by dissolving the dicephalic peptide amphiphile at double the desired final hydrogel concentration in aqueous solution (water, phosphate buffered saline etc.) having a pH from about 5 to about 9, followed by mixing with physiological salt solutions (such as phosphate buffered saline, Hank's balanced salt solution, Dulbecco's Modified Eagle media), cell media (mixtures of aforementioned physiological salt solutions and serum) or physiological fluids (such as synovial fluid, spinal fluid). In another embodiment, hydrogels that display shear-thinning behavior are prepared directly by dissolving the dicephalic peptide amphiphile in physiological salt solutions. Final dicephalic peptide amphiphile concentrations can range from about 1 percent by weight up to the limit of solubility. The concentration of ions should be such that it is sufficient to neutralize the charges in the solubility enhancing region. In one embodiment, a four weight percent dicephalic peptide amphiphile solution in water and a 1:1 mixing ratio with physiological salt solution is used, although other ratios may be used as long as the concentration of ions is sufficient to neutralize the charge of the solubility enhancing region of the peptide. In water, the electrostatic repulsion between the terminal acid groups partially counter-acts the self-assembly, leading to small assemblies. Gelation occurs upon mixing because the ions screen the surface charge resulting in fiber elongation followed by gelation. Rheological comparison showed that salt concentration affects the kinetics of formation.

In an alternative embodiment, the dicephalic peptide amphiphile can be dissolved by selecting the pH such that the terminal amino acid is charged. Gelation can then be induced by modifying the pH such that the charge of the terminal amino acid in the solubility enhancing region becomes neutralized.

In yet another embodiment, two or more dicephalic peptide amphiphiles with different peptide sequences are mixed and induce to gel with any of the described methods. One can mix in DPAs that do not form gels on their own as long as they are the minority component (<50% of total DPA).

Mixing in a 1:1 ratio at physiological concentrations of divalent ions leads to gel formation in 40-60 seconds. When PBS is used, gelation occurs in 2-3 minutes at concentrations >4 weight %, whereas at supraphysiological divalent ion concentrations gelation is immediate. Finally, when the gel is vortexed, the formulation liquefies and re-forms the gel in 3-5 minutes. Increasing the final concentration of DPA from 1 to 2 to 4 weight percent leads to an order of magnitude increase in rheological properties in each step. Therefore, matching between the polar amino acids in the solubility enhancing region and the ion concentration predominantly controls kinetics of formation whereas the nature of the self-assembling region (hydrogen bonding only vs. pi-pi stacking) and molecule concentration control the final rheological properties. The rheological properties of the gel keep improving over time, reflecting the dynamic nature of the gel: the initial kinetically trapped structure re-organizes in the thermodynamically more stable form. After 30-60 minutes, a structure close to optimal seems to have been achieved.

Comparison of the various polar, non-charged amino acids in the solubility enhancing regions in a kinetics of formation experiment shows that the Asn-Asn-Ser (SEQ ID NO: 29) sequence achieves the highest rheological properties followed by Gln-Gly-Ser (SEQ ID NO: 30) and finally Gln-Gln-Ser (SEQ ID NO: 28). However, at a strain sweep experiment, the Asn-Asn-Ser (SEQ ID NO: 29) gel starts breaking down at 40% strain whereas the other two gels can handle almost 100% strain.

The dicephalic hydrogels prepared as described above are useful for the delivery of bioactive agents including, but not limited to cells, proteins, and oligonucleotides in a minimally invasive fashion. The benign mechanism of cross-linking does not interfere with the biological function of the incorporated active whereas the low viscosity of the gel precursor solution allow for introduction in a minimally invasive fashion. Dicephalic peptide amphiphile hydrogels that are extended with bioactive sequences might also be useful to capture circulating bioactives, perform signaling events, modulate cell behavior such as factor secretion etc.

Suitable cell types that could be encapsulated include, but are not limited to stem cells, progenitor cells, primary cells, transfected cells and immortalized cells. In one embodiment, human umbilical tissue derived cells were encapsulated. In another embodiment, human kidney derived cells were encapsulated. In yet another embodiment, human mammary artery cells were encapsulated. In addition, tissue fragments or minced tissue can be encapsulated. Suitable proteins include, but are not limited to antibodies and growth factors. Suitable oligonucleotides, include but are not limited to siRNA and microRNA.

For example, delivery of cells can be achieved by mixing the dissolved dicephalic peptide amphiphile at double the final concentration in a 1:1 ratio with a cell suspension in the cell appropriate media. In one embodiment, 100 microliters of a 4 weight % dicephalic peptide amphiphile solution is mixed with 100 microliters of a cell suspension containing 100,000 cells. Cell concentrations are limited by the maximum cell density in the cell suspension. In one embodiment, the number of cells encapsulated in the gel range from about 10,000 cells to about 1,000,000 cells. There is no appreciable reduction of cell viability over the course of three weeks for a variety of cell types.

Delivery of the cell containing formulations in vivo can be achieved in a number of ways. Not limiting the possibilities, one could use a dual barreled syringe with one chamber containing the dicephalic peptide amphiphile solution in water and the other chamber containing the cell suspension. One can then either use a single or dual lumen cannula depending on where one wants mixing to occur. Alternatively, one can make use of the shear-thinning properties and pre-form the gel in a single barrel syringe. Upon injection, the gel will shear-thin and pass through the cannula after which it re-forms in vivo.

In one embodiment, biocompatibility of three different formulations, Val-Ala-Val-Ala-Val-Ala-Glu-Gly-Glu (SEQ ID NO: 39), Gly-Phe-Gly-Phe-Gly-Phe-Gly-Glu-Gly-Glu (SEQ ID NO: 5) and Gly-Phe-Gly-Phe-Gly-Phe-Gly-Gln-Gly-Gln (SEQ ID NO: 40) was evaluated by injecting 100 microliter of gel into a pocket that was created in the intragluteal muscle. After 28 days, no gel could be detected in any of the groups. Over the course of the experiment, the Gly-Phe-Gly-Phe-Gly-Phe-Gly-Gln-Gly-Gln (SEQ ID NO: 40) formulation showed no tissue response. However, the other two formulations, requiring supraphysiological calcium concentration to gel, showed necrosis of the underlying muscle tissue.

EXAMPLES

Please note that all weight percentages described herein are weight to weight (w/w) unless otherwise indicated.

Example 1

Synthesis of the Dicephalic Tail

Figure 2:
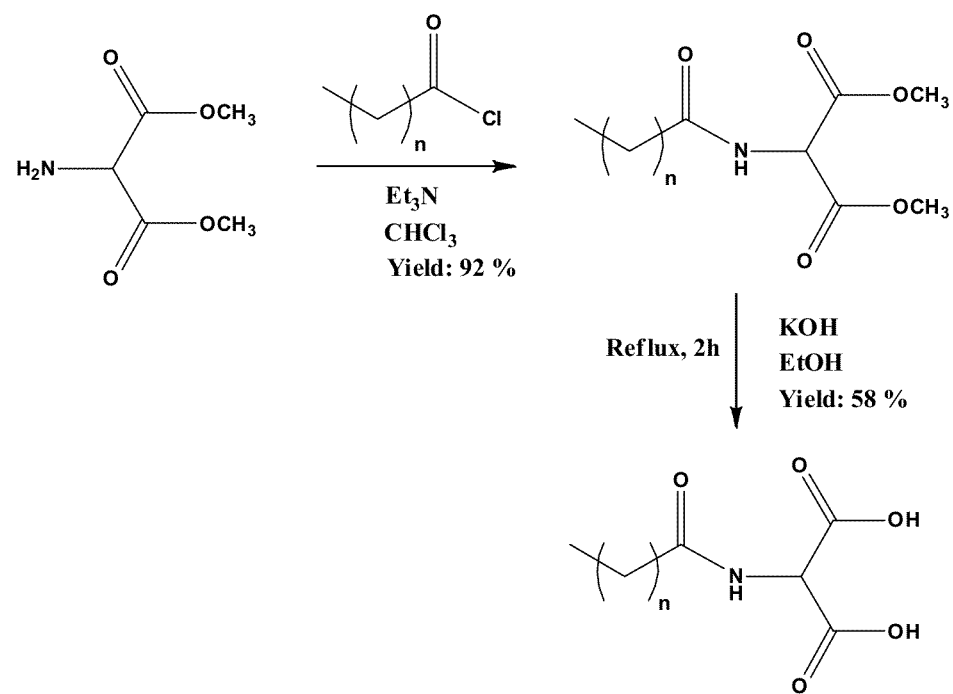
FIG. 2. Schematic of dicephalic tail synthesis.

The synthesis of the tail was performed on a multi-gram scale (~5 g starting material) and starts from the methyl ester of 2-amino-malonic acid and palmitoyl chloride (FIG. 2). The coupling of palmitoyl chloride to 2-amino-malonic acid in chloroform was achieved in 92% yield. The product was purified by subsequent extractions with hydrochloric acid, 10% sodium bicarbonate and water. Subsequently, ester hydrolysis in ethanol was performed by reflux for 2 hours in the presence of excess potassium hydroxide. Purification was performed by a series of extractions with hydrochloric acid, saturated sodium chloride solution and water. The organic layer was dried with magnesium sulfate but this caused the formation of a gel-like mixture rather than the standard magnesium sulfate hydrate precipitate. Attempts to filter of the magnesium sulfate hydrate were unsuccessful. Therefore, the mixture was triturated with water to remove the magnesium sulfate hydrate, followed by filtering of the precipitate and washing the precipitate with diethyl ether to remove trace amounts of water. The final yield of the dicephalic tail was 56%.

Example 2

Manual Solid Phase Peptide Synthesis

Starting from 0.25 mmol pre-loaded Wang resin (100-200 mesh), the resin was swollen in dichloromethane for 1 hour in a peptide synthesis vessel. Subsequently, a cycle of deprotection and amino acid coupling steps was repeated until all amino acid residues were coupled. Deprotection was achieved by adding 5 cc of 20% piperidine in dimethylformamide (DMF) and shaking for 5 minutes followed by draining the deprotection cocktail. This was repeated twice for a total of three deprotection steps. After an N-methylpyrrolidone (NMP) wash, coupling was performed by dissolving 1 mmol (2-(1H-Benzotriazol-1-yl)-1,1,3,3-tetramethyluronium hexafluorophosphate) (HBTU) in 5 cc NMP which was subsequently added to 1 mmol amino acid. The mixture was incubated room temperature for 5 minutes after which 0.3 cc diisopropylethylamine was added. The mixture was then added to the resin and shaken for 1 hour. After an NMP wash, the next cycle was performed.

After all amino acids were added, the tail was added by the following procedure. 70 mg HBTU was dissolved in 5 cc NMP and added to 40 mg tail (prepared as described in Example 1). The mixture was sonicated briefly to facilitate dissolution of the tail. Next, 0.1 cc diisopropylethylamine was added and the mixture was added to the resin containing the peptide in a peptide synthesis vessel. After shaking for 18 hours, the coupling mixture was drained and fresh mixture was added followed by an additional shaking for 18 hours. After draining the coupling mixture, the resin was washed with NMP followed by two washes with dichloromethane. The resin was allowed to dry overnight.

Deprotection of the side chains and cleavage from the resin was achieved by shaking for 3 hours with 10 cc of 95% trifluoroacetic acid (TFA)/2.5% triisopropylsilane/2.5% water. Next, the TFA mixture was drained from the peptide synthesis vessel and collected in a round bottom flask. The resin was washed twice with 1 cc TFA and the fractions were combined. After evaporation of the TFA until a minimal volume remained, the dicephalic peptide amphiphile was precipitated with a 10-fold excess of cold diethyl ether. The dicephalic peptide amphiphile was collected by filtration. Subsequently the peptide was dissolved in 10-20 cc water by pH adjustment. Once the dicephalic peptide amphiphile was completely dissolved, the pH was adjusted to 6-8, after which the dicephalic peptide amphiphile was lyophilized.

Example 3

Automated Solid Phase Peptide Synthesis

Automated synthesis was performed on an Focus XC synthesizer (AAPPTEC, Louisville, Ky.) on a 0.25 mmol scale starting from pre-loaded Wang resin (100-200 mesh). The resin was swollen for 15 minutes in NMP. Deprotection was performed in two steps, first a three minute incubation with 20% piperidine in DMF followed by a 10 minute incubation with 20% piperidine in DMF. After 6 washes with NMP, coupling was performed by pre-mixing 3.7 cc of 0.2M amino acid solution and 0.2M HBTU in NMP followed by the addition of 2.4 cc of diisopropylethylamine. The mixture was then added to the resin and shaken for 30 minutes. After 6 NMP washes the next cycle was performed.

After all amino acids were added, the tail was added by the following procedure. 70 mg HBTU was dissolved in 5 cc NMP and added to 40 mg tail (prepared as described in Example 1). The mixture was sonicated briefly to facilitate dissolution of the tail. Next, 0.1 cc diisopropylethylamine was added and the mixture was added to the resin containing the peptide in a peptide synthesis vessel. After shaking for 18 hours, the coupling mixture was drained and fresh mixture was added followed by an additional shaking for 18 hours. After draining the coupling mixture, the resin was washed with NMP followed by two washes with dichloromethane. The resin was allowed to dry overnight.

Deprotection of the side chains and cleavage from the resin was achieved by shaking for 3-4 hours with 10 cc 95% trifluoroacetic acid(TFA)/2.5% triisopropylsilane/2.5% water. Next, the TFA mixture was drained from the peptide synthesis vessel and collected in a round bottom flask. The resin was washed twice with 1 cc TFA and the fractions were combined. After evaporation of the TFA until a minimal volume remained, the peptide was precipitated with a 10-fold excess of cold diethyl ether. Alternatively, the TFA was completely removed and the residual dicephalic peptide amphiphile was triturated for 30 minutes with 50 cc diethylether. The dicephalic peptide amphiphile was collected by filtration. Subsequently the dicephalic peptide amphiphile was dissolved in 10-20 cc water by pH adjustment. Once the dicephalic peptide amphiphile was completely dissolved, the pH was adjusted to 6-8, after which the dicephalic peptide amphiphile was lyophilized.

The dicephalic peptide amphiphiles (DPAs) having the peptide sequences shown in Table 1 have been synthesized using the methods described above in Examples 1-3.

TABLE 1

| SEQ ID NO: | Peptide Sequence (X in Formula 1) | Manual synthesis | Automated Synthesis |
|---|---|---|---|
| 1 | Val-Ala-Val-Ala-Val-Ala-Lys-Ala | Yes | No |
| 2 | Phe-Gly-Phe-Gly-Phe-Gly-Lys-Ala | Yes | No |
| 3 | Val-Ala-Val-Ala-Val-Ala-Glu-Glu-Glu | Yes | No |
| 4 | Gly-Val-Ala-Val-Ala-Val-Ala-Glu-Gly-Glu | Yes | No |
| 5 | Gly-Phe-Gly-Phe-Gly-Phe-Gly-Glu-Gly-Glu | Yes | Yes |
| 6 | Gly-Phe-Gly-Phe-Gly-Phe-Gly-Phe-Gly-Glu-Gly-Glu | No | Yes |
| 7 | Gly-Trp-Gly-Trp-Gly-Trp-Gly-Glu-Gly-Glu | No | Yes |
| 8 | Gly-Phe-Gly-Phe-Gly-Phe-Gly-Gln-Gln-Ser | No | Yes |
| 9 | Gly-Trp-Gly-Trp-Gly-Trp-Gly-Gln-Gln-Ser | No | Yes |
| 10 | Gly-Tyr-Gly-Tyr-Gly-Tyr-Gly-Gln-Gln-Ser | No | Yes |
| 11 | Gly-Phe-Gly-Phe-Gly-Phe-Gly-Asn-Asn-Ser | No | Yes |
| 12 | Gly-Phe-Gly-Phe-Gly-Phe-Gly-Gln-Gly-Ser | No | Yes |
| 13 | Gly-Phe-Gly-Phe-Gly-Phe-Gly-Gly-Gln-Ser | No | Yes |
| 14 | Gly-Phe-Gly-Phe-Gly-Phe-Gly-Asn-Gly-Ser | No | Yes |
| 15 | Gly-Phe-Gly-Phe-Gly-Phe-Gly-Gly-Asn-Ser | No | Yes |
| 16 | Gly-Phe-Gly-Phe-Gly-Phe-Gly-Glu-Gly-Ser | No | Yes |
| 17 | Gly-Phe-Gly-Phe-Gly-Phe-Gly-Lys-Gly-Ser | No | Yes |

The peptide sequences shown in Table 2 were used for the self-assembly inducing region.

TABLE 2

| SEQ ID NO: | Peptide Sequence (self-assembly inducing region) |
|---|---|
| 18 | Val-Ala-Val-Ala-Val-Ala |
| 19 | Gly-Val-Ala-Val-Ala-Val-Ala |
| 20 | Phe-Gly-Phe-Gly-Phe-Gly |
| 21 | Gly-Phe-Gly-Phe-Gly-Phe-Gly |
| 22 | Gly-Phe-Gly-Phe-Gly-Phe-Gly-Glu-Gly |
| 23 | Gly-Trp-Gly-Trp-Gly-Trp-Gly |
| 24 | Gly-Tyr-Gly-Tyr-Gly-Tyr-Gly |

The peptide sequences used for the solubility enhancing region are shown in Table 3.

TABLE 3

| SEQ ID NO: | Peptide Sequence (solubility enhancing region) |
|---|---|
| 25 | Lys-Ala |
| 26 | Glu-Glu-Glu |
| 27 | Glu-Gly-Glu |
| 28 | Gln-Gln-Ser |
| 29 | Asn-Asn-Ser |
| 30 | Gln-Gly-Ser |
| 31 | Gly-Gln-Ser |
| 32 | Asn-Gly-Ser |
| 33 | Gly-Asn-Ser |
| 34 | Glu-Gly-Ser |
| 35 | Lys-Gly-Ser |

For comparison purposes, a linear peptide amphiphile analogue to the DPA with SEQ ID NO 8 similar to those reported in the art was created by the automated synthesis route as described in Example 2 with the modification that palmitoyl acid was used as the tail in a 1:1 molar ratio to the peptide on the resin instead of the dicephalic tail. In addition, the Gly-Phe-Gly-Phe-Gly-Phe-Gly-Gln-Gln-Ser (SEQ ID NO: 8) peptide was prepared by automated peptide synthesis.

Example 4

Gelation Experiments

Figure 3A:
FIG. 3A. Self-supporting gels of 2 wt % Gly-Phe-Gly-Phe-Gly-Phe-Gly-Gln-Gln-Ser (SEQ ID NO: 8) DPA in DMEM in a vial.
Figure 3B:
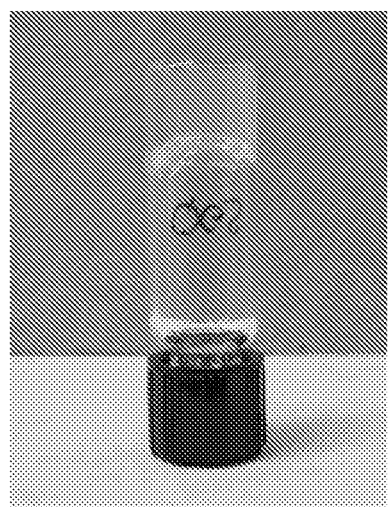
FIG. 3B. Self-supporting gels of 2 wt % Gly-Phe-Gly-Phe-Gly-Phe-Gly-Gln-Gln-Ser (SEQ ID NO: 8) DPA in DMEM in the vial now inverted.

Inversion tests were performed to determine qualitatively under which conditions the various DPAs formed self-supporting hydrogels. The various types of DPAs were tested by dissolving them in ultrapure water (>18 MΩ resistivity) at double the desired final concentration followed by mixing in a 1:1 ratio with different liquid mediums. Gelation was deemed to have occurred if the gel supported its own weight upon inverting the vial (FIG. 3A and FIG. 3B). Gelation was tested at final concentrations of 1, 2 and 4 weight percent. We tested phosphate buffered saline (PBS), and Dulbecco's modified eagle media (DMEM) as liquid medium. Typical scale is 100 µl each of DPA solution in water and mixing medium but other scales have been tested. Finally, if no spontaneous gelation occurs, 10 µl of 100 mg/cc calcium chloride solution was added to induce gelation. The DPAs having peptide sequences of Val-Ala-Val-Ala-Val-Ala-Lys-Ala (SEQ ID NO: 1) and Phe-Gly-Phe-Gly-Phe-Gly-Lys-Ala (SEQ ID NO: 2) could not be solubilized in the ultrapure water and therefore were not tested.

Comparison of Hydrogen-Bonding Sequences to pi-pi Stacking Sequences

The Val-Ala-Val-Ala-Val-Ala-Glu-Glu-Glu (SEQ ID NO: 3) and Gly-Val-Ala-Val-Ala-Val-Ala-Glu-Gly-Glu (SEQ ID NO: 4) DPAs formed gels at minimal concentrations of 2 weight percent in DMEM with calcium added, whereas the Gly-Phe-Gly-Phe-Gly-Phe-Gly-Glu-Gly-Glu (SEQ ID NO: 5) DPA formed a gel at a minimal concentration of 1 weight percent (Table 4). Gels were self-supporting when inverted to mix, optically transparent and after two months had not disintegrated nor expelled water. After this finding, supported by rheology (vide supra), self-assembly inducers based on aromatic amino acids were used exclusively.

TABLE 4

| Dicephalic Peptide Amphiphile | Water | DMEM | Calcium added |
|---|---|---|---|
| Gly-Val-Ala-Val-Ala-Val-Ala-Glu-Glu-Glu (SEQ ID NO: 41) | No | No | Yes, 2 wt % |
| Gly-Val-Ala-Val-Ala-Val-Ala-Glu-Gly-Glu (SEQ ID NO: 4) | No | No | Yes, 2 wt % |
| Phe-Gly-Phe-Gly-Phe-Gly-Glu-Gly-Glu (SEQ ID NO: 42) | No | No | Yes, 1 wt % |

Use of a Polar, Non-Charged Solubility Enhancing Region

The Gly-Phe-Gly-Phe-Gly-Phe-Gly-Gln-Gln-Ser (SEQ ID NO: 8) DPAs form self-supporting gels at 4 wt % in water after approx. 5 minutes. These gels can be disrupted by vortexing, after which they reform when left alone. Similarly, qualitatively better gels can be prepared by dissolving them in PBS rather than water. When mixed with DMEM, these DPAs form gels at 2 wt % without addition of supplemental calcium ions (Table 5). It is postulated that using polar, non-charged amino acids in the solubility enhancing region removes the need for extra calcium and allows for gelation at physiological salt concentrations.

TABLE 5

| Dicephalic Peptide Amphiphile | Water | PBS | DMEM |
|---|---|---|---|
| Gly-Phe-Gly-Phe-Gly-Phe-Gly-Gln-Gln-Ser (SEQ ID NO: 8) | Yes, 4 wt % | Yes, 4 wt % | Yes, 2 wt % |

Variation of Aromatic Amino Acids in Self-Assembly Inducing Region.

The Gly-Trp-Gly-Trp-Gly-Trp-Gly-Gln-Gln-Ser (SEQ ID NO: 9) DPA was prepared since it was anticipated that a larger aromatic moiety would provide stronger pi-pi stacking interactions. However, both in the case of Gly-Trp-Gly-Trp-Gly-Trp-Gly-Gln-Gln-Ser (SEQ ID NO: 9) and Gly-Trp-Gly-Trp-Gly-Trp-Gly-Gln-Gln-Ser (SEQ ID NO: 9) DPAs, no gelation was observed under conditions tested (2-4 wt %, water, PBS, DMEM and DMEM plus calcium). Gly-Tyr-Gly-Tyr-Gly-Tyr-Gly-Gln-Gln-Ser (SEQ ID NO: 10) DPA does form gels when mixed with DMEM and calcium but does not gel in water, PBS or DMEM (Table 6). Therefore, it was concluded that phenylalanine is the preferred residue in terms of the efficiency of aromatic stacking. Tryptophan and Tyrosine may still work at different spacing between the aromatic amino acids.

TABLE 6

| Dicephalic Peptide Amphiphile | Water | PBS | DMEM | Calcium added |
|---|---|---|---|---|
| Gly-Phe-Gly-Phe-Gly-Phe-Gly-Gln-Gln-Ser (SEQ ID NO: 8) | Yes, 4% | Yes, 4% | Yes, 2% | |
| Gly-Trp-Gly-Trp-Gly-Trp-Gly-Gln-Gln-Ser (SEQ ID NO: 9) | No | No | No | No |
| Gly-Tyr-Gly-Tyr-Gly-Tyr-Gly-Gln-Gln-Ser (SEQ ID NO: 10) | No | No | No | Yes, 2% |

Variation of Amino Acid Sequence in the Solubility Enhancing Region.

Gly-Phe-Gly-Phe-Gly-Phe-Gly-Asn-Asn-Ser (SEQ ID NO: 11) DPA was prepared to see whether a shorter side chain would be beneficial. This DPA displays similar gelation characteristics compared to Gly-Phe-Gly-Phe-Gly-Phe-Gly-Gln-Gln-Ser (SEQ ID NO: 8) DPA. In addition, Gly-Phe-Gly-Phe-Gly-Phe-Gly-Gln-Gly-Ser (SEQ ID NO: 12) DPA was prepared to test whether reduced intramolecular steric hindrance would be beneficial. The gel formed more rapidly and appears to be stronger. Further permutations were made, including Gly-Phe-Gly-Phe-Gly-Phe-Gly-Gly-Gln-Ser (SEQ ID NO: 13), Gly-Phe-Gly-Phe-Gly-Phe-Gly-Asn-Gly-Ser (SEQ ID NO: 14) and Gly-Phe-Gly-Phe-Gly-Phe-Gly-Gly-Asn-Ser (SEQ ID NO: 15) (Table 7). All of these gels displayed similar gelation characteristics demonstrating that any permutation of Gln, Asn and Gly lead to gels that can form upon mixing with DMEM.

TABLE 7

| Dicephalic peptide amphiphile | Water | PBS | DMEM |
|---|---|---|---|
| Gly-Phe-Gly-Phe-Gly-Phe-Gly-Gln-Gln-Ser (SEQ ID NO: 8) | Yes, 4% | Yes, 4% | Yes, 2% |
| Gly-Phe-Gly-Phe-Gly-Phe-Gly-Asn-Asn-Ser (SEQ ID NO: 11) | Yes, 2% | Yes, 4% | Yes, 2% |
| Gly-Phe-Gly-Phe-Gly-Phe-Gly-Gln-Gly-Ser (SEQ ID NO: 12) | No | Yes, 2% | Yes, 2% |

TABLE 7-continued

| Dicephalic peptide amphiphile | Water | PBS | DMEM |
|---|---|---|---|
| Gly-Phe-Gly-Phe-Gly-Phe-Gly-Gly-Gln-Ser (SEQ ID NO: 13) | No | No | Yes, 2% |
| Phe-Gly-Phe-Gly-Phe-Gly-Asn-Gly-Ser (SEQ ID NO: 43) | No | No | Yes, 2% |
| Gly-Phe-Gly-Phe-Gly-Phe-Gly-Gly-Asn-Ser (SEQ ID NO: 15) | No | No | Yes, 2% |

Comparison of Dicephalic Amphiphiles to Linear Amphiphiles and Peptides.

Both the peptide and linear peptide amphiphile analogue were compared to the dicephalic peptide amphiphile molecule (Table 8). The peptide did not form any gels under any of the conditions tested. The linear peptide amphiphile analogue did not form gels in water, PBS or when mixed with DMEM but could be gelled when supraphysiological concentrations of calcium was provided. This result demonstrated the benefits of the dicephalic architecture to achieve the properties described above and presumably reflects the lower critical aggregation concentrations of dicephalic amphiphiles.

TABLE 8

| Molecule | Water | PBS | DMEM | Calcium added |
|---|---|---|---|---|
| Gly-Phe-Gly-Phe-Gly-Phe-Gln-Gln-Ser(peptide) (SEQ ID NO: 8) | No | No | No | No |
| Gly-Phe-Gly-Phe-Gly-Phe-Gly-Gln-Gln-Ser(linear) (SEQ ID NO: 8) | No | No | No | Yes, 2% |
| Gly-Phe-Gly-Phe-Gly-Phe-Gly-Gln-Gln-Ser(DPA) (SEQ ID NO: 8) | Yes, 4% | Yes, 4% | Yes, 2% | |

Example 5

Titration of Dicephalic Peptide Amphiphile Acid Groups with Calcium Ions

Figure 4:
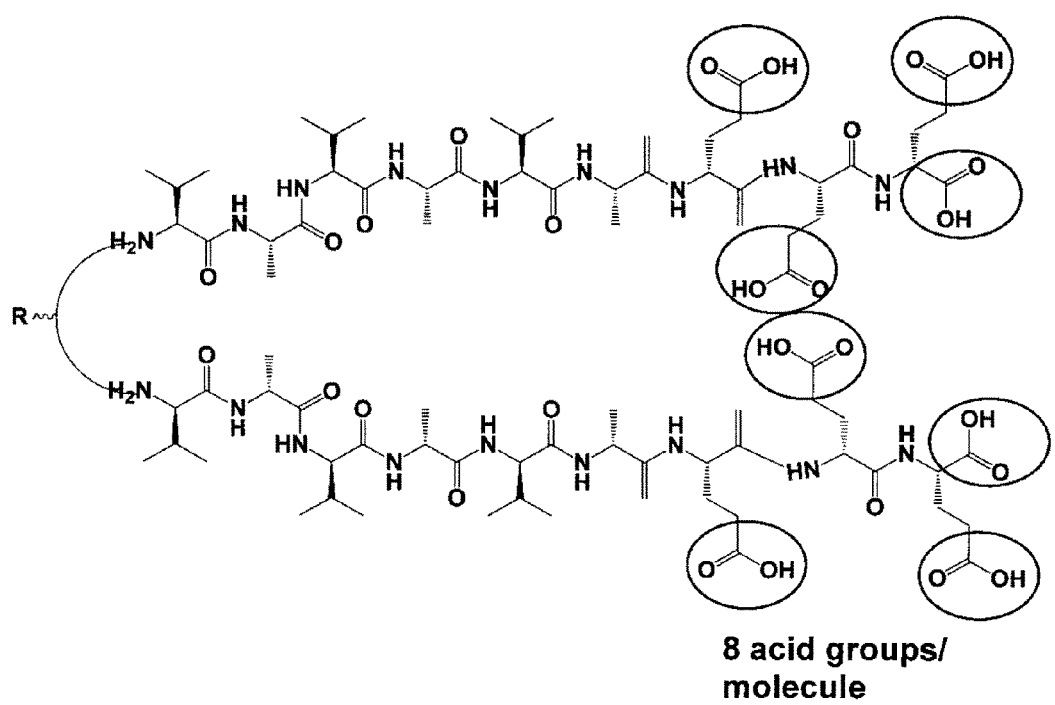
FIG. 4. Chemical structure depicting possible calcium binding groups of Val-Ala-Val-Ala-Val-Ala-Glu-Glu-Glu (SEQ ID NO: 3) DPA.

The Val-Ala-Val-Ala-Val-Ala-Glu-Glu-Glu (SEQ ID NO: 3) DPA was titrated with calcium ions to determine the number of acid groups that required ion complexation in order for gelation to occur. Theoretically, there are eight acid groups (four per head group) that could be involved in the gelation process (FIG. 4). Titrating down from 16 to 1 equivalent by halving the amount of calcium showed that the transition point between stable gel formation and no or weak gel formation occurred between two and one equivalent of calcium.

Example 6

Rheology to Evaluate the Mechanical Properties of DPA Hydrogels

Oscillating rheology by the parallel plates method (radius=25 mm) was performed on 400 μl gels to assess the mechanical strengths of gels. Time sweeps were performed to evaluate kinetics of formation at a constant strain rate of 1% and frequency of 1 rad/s. Strain sweeps were performed ranging from 1-100% strain in increments of 2% at a constant frequency of 1 rad/s. Cross-over of G' and G" was used to determine the gel point and point of breakdown. Time sweeps were initiated immediately after mixing the solutions that lead to DPA hydrogel formation. In the strain sweeps, the gels were allowed to form on the plate for 30 minutes before the measurement is initiated.

Comparison of Aromatic Vs. Non-Aromatic Self-Assembly Inducing Regions

Figure 5:
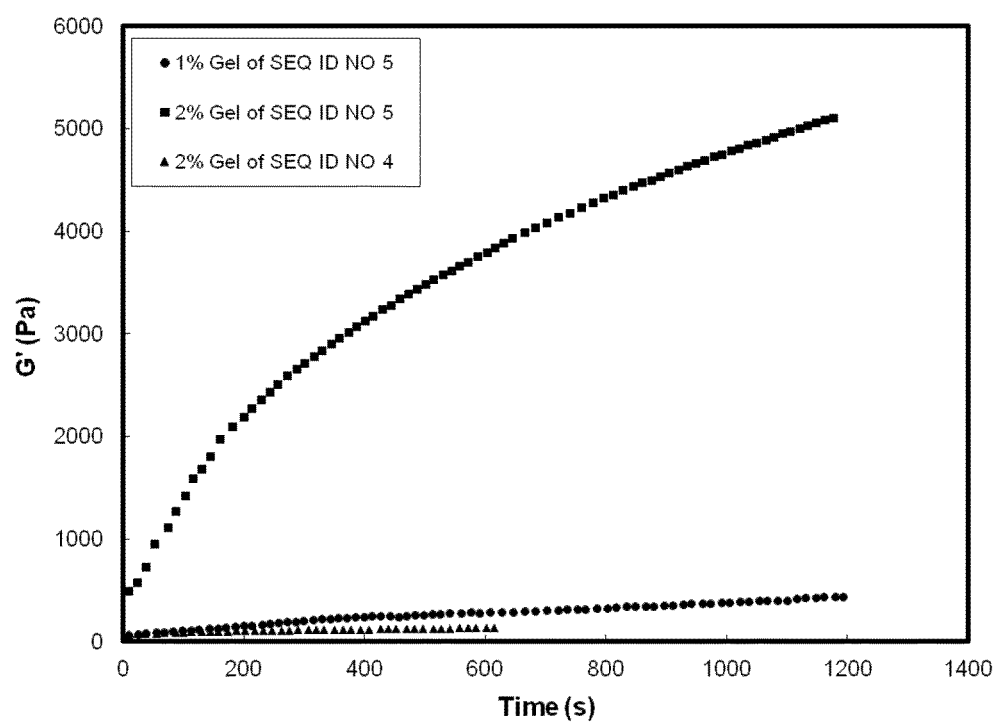
FIG. 5. Comparison of G' for the hydrogels with Glu-Gly-Glu (SEQ ID NO: 27) sequence in the solubility enhancing region and self-assembly inducing regions containing either beta-sheet type hydrogen-bonding units or pi-pi stacking units.

Time sweeps of 1 wt % and 2 wt % Gly-Phe-Gly-Phe-Gly-Phe-Gly-Glu-Gly-Glu (SEQ ID NO: 5) DPA and 2 wt % Gly-Val-Ala-Val-Ala-Val-Ala-Glu-Gly-Glu (SEQ ID NO: 4) DPA were performed. The gelation process was initiated on the plate at 25° C. by the addition of 10 μl of 100 mg/ml calcium chloride solution to a solution of the DPA in DMEM. In all three cases, the cross-over point between G' and G", which defines the gel point, occurred before measurement started. Extrapolation of the curves gives an estimate of 45-50 seconds for the gel point. The G" curve remains flat after 1 minute, but G' keeps increasing for at least one hour showing the dynamic nature of the gel which allows re-arrangement from the initial kinetic structure to the thermodynamically favored structure (FIG. 5). The G' of the 2 wt % Gly-Phe-Gly-Phe-Gly-Phe-Gly-Glu-Gly-Glu (SEQ ID NO: 5) DPA gel is an order of magnitude larger (4,000 Pa after 10 minutes) than the 1 wt % Gly-Phe-Gly-Phe-Gly-Phe-Gly-Glu-Gly-Glu (SEQ ID NO: 5) DPA (300 Pa) and the 2 wt % Gly-Val-Ala-Val-Ala-Val-Ala-Glu-Gly-Glu (SEQ ID NO: 4) DPA (140 Pa). After 1 hour, the 2 wt % Gly-Phe-Gly-Phe-Gly-Phe-Gly-Glu-Gly-Glu (SEQ ID NO: 5) gel has achieved a strength of 7,200 Pa and further extrapolation of the curve gives an estimated final strength of ~10,000 Pa. After 1 hour, the temperature was raised to 37° C., which resulted in a drop of G' to 5,000 Pa because of increased mobility but the gel started to recover strength immediately. This experiment demonstrates that the use of pi-pi stacking interactions in the self-assembly inducing region results in stronger gels. In addition, a doubling of final dicephalic peptide amphiphile concentration leads to an approximately ten-fold increase in mechanical properties.

Figure 6:
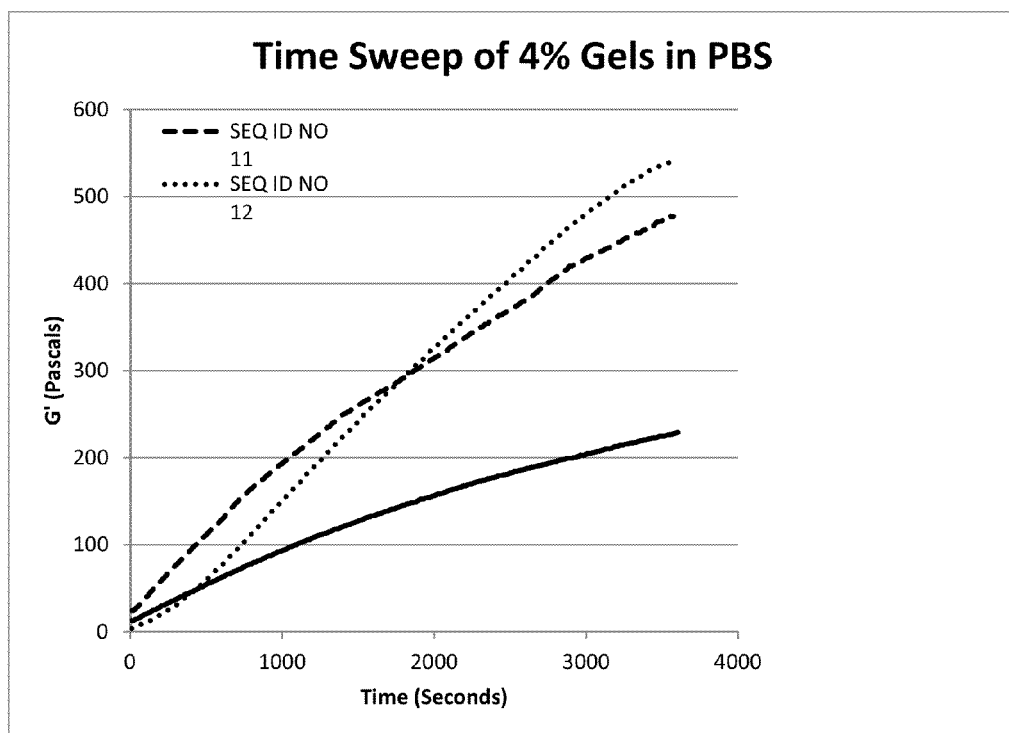
FIG. 6. Time sweep comparison of gels with different polar, non-charged amino acids in the solubility enhancing region in PBS.

Time Sweep Comparison of Gels with Polar Non-Charged Amino Acids in the Solubility Enhancing Region in PBS Time sweeps were performed on 4 wt % Gly-Phe-Gly-Phe-Gly-Phe-Gly-Gln-Gln-Ser (SEQ ID NO: 8), Gly-Phe-Gly-Phe-Gly-Phe-Gly-Gln-Gly-Ser (SEQ ID NO: 12) and Gly-Phe-Gly-Phe-Gly-Phe-Gly-Asn-Asn-Ser (SEQ ID NO: 11) gels in DMEM. All samples had transition points before measurement had started. As can be seen in FIG. 6, the gels keep gradually improving in properties. The order of gel strength appears to be DPA with Asn-Asn-Ser>Gln-Gly-Ser>Gln-Gln-Ser (SEQ ID NOS 29, 30 and 28, respectively, in order of appearance) sequence in the solubility enhancing region.

Figure 7:
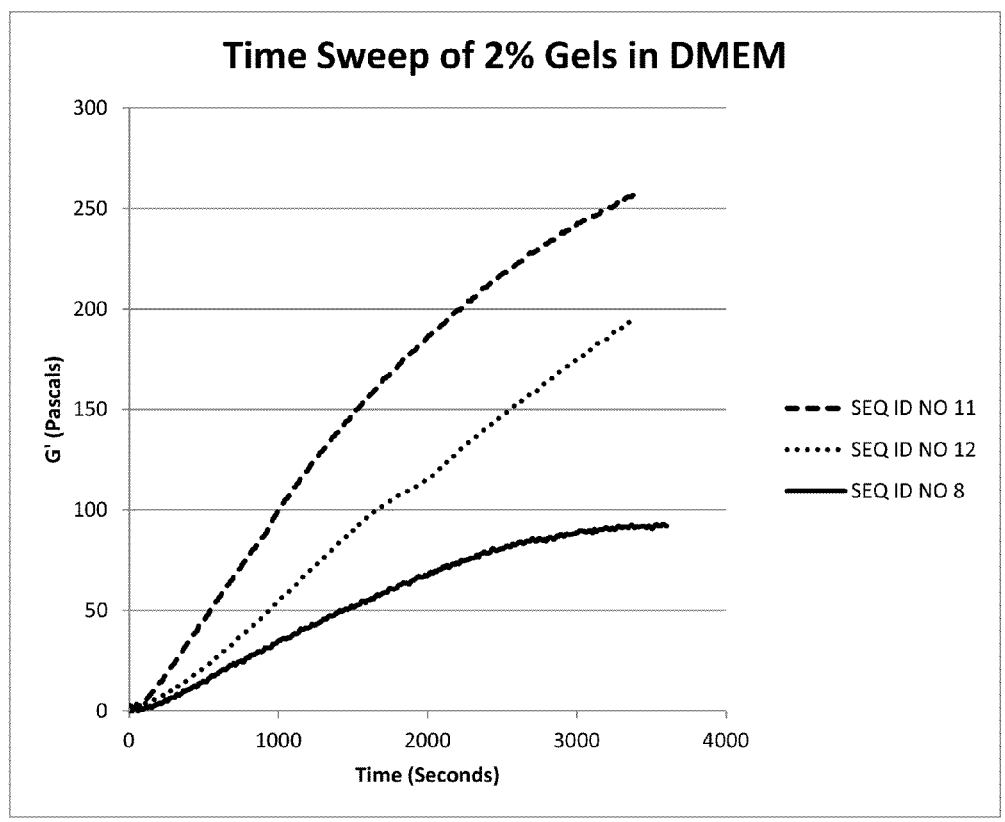
FIG. 7. Time sweep comparison of different polar, non-charged amino acids in the solubility enhancing region in DMEM.

Time Sweep Comparison of Gels with Polar Non-Charged Amino Acids in the Solubility Enhancing Region in DMEM Time sweeps were performed on 2 wt % Gly-Phe-Gly-Phe-Gly-Phe-Gly-Gln-Gln-Ser (SEQ ID NO: 8), Gly-Phe-Gly-Phe-Gly-Phe-Gly-Gln-Gly-Ser (SEQ ID NO: 12) and Gly-Phe-Gly-Phe-Gly-Phe-Gly-Asn-Asn-Ser (SEQ ID NO: 11) gels in DMEM (FIG. 7). In these samples, the gel point occurred instantaneous for the DPAs with Gln-Gly-Ser (SEQ ID NO: 30) and Asn-Asn-Ser (SEQ ID NO: 29) sequences and at 74 seconds after mixing for the DPA with Gln-Gln-Ser (SEQ ID NO: 28) sequence. The gels keep improving in properties and the order of strength in terms of DPA sequence in the solubility enhancing region is Asn-Asn-Ser>Gln-Gly-Ser>Gln-Gln-Ser (SEQ ID NOS 29, 30 and 28, respectively, in order of appearance).

Figure 8:
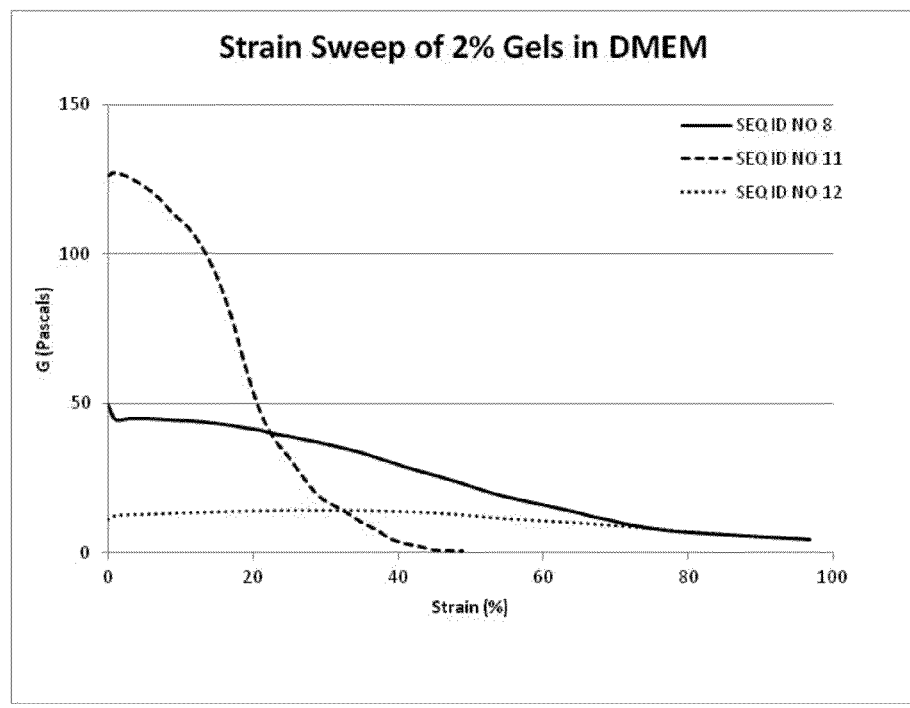
FIG. 8. Strain sweep comparison of different polar, non-charged amino acids in the solubility enhancing region in DMEM.

Strain Sweep Comparison of Gels with Polar Non-Charged Amino Acids in the Solubility Enhancing Region in DMEM Strains sweeps were performed on 2 wt % Gly-Phe-Gly-Phe-Gly-Phe-Gly-Gln-Gln-Ser (SEQ ID NO: 8), Gly-Phe-Gly-Phe-Gly-Phe-Gly-Gln-Gly-Ser (SEQ ID NO: 12) and Gly-Phe-Gly-Phe-Gly-Phe-Gly-Asn-Asn-Ser (SEQ ID NO: 11) gels in DMEM (FIG. 8). Gels were allowed to form for 30 minutes before the experiment was initiated. As can be seen in FIG. 8, the DPA gel with the Asn-Asn-Ser (SEQ ID NO: 29) sequence in the solubility enhancing region had the highest initial strength, but showed a more rapid decline in properties (decline starts at 15% strain rather than 33 and 50%) and re-crossed the transition point before the others (42% strain rather than 99% strain).

Example 7

Cell Viability and Proliferation Experiment

Cell Viability and Proliferation Experiment with hUTC Cells in DPA Gels.

The viability and proliferation of cells in the gels was evaluated by encapsulating human umbilical cord cells (hUTCs) in the gels. hUTCs were isolated as described in U.S. Pat. No. 7,510,873. Cells were thawed from storage and cultured for four days in Hayflick media. After four days, the cells were trypsinized and counted by the Guava ViaCount methodology (Millipore, Billerica, Mass.). Cells were re-suspended in Hayflick media at a density of 1,000,000 cells/ml. Encapsulation of the cells in the gels was achieved by adding 100 µl cell suspension to 100 µl of a 4 wt % DPA solution in ultrapure in a 24 well plate, resulting in a final DPA concentration of 2%. The gels were incubated for 1 h at 37° C., 5% $CO_2$ after which 1000 µl media was added on top of the gel. Cells were incubated at 37° C., 5% $CO_2$. Every 3-4 days of culture, 500 µl media was replaced.

Cell experiments with Gly-Val-Ala-Val-Ala-Val-Ala-Glu-Gly-Glu (SEQ ID NO: 4) and Gly-Phe-Gly-Phe-Gly-Phe-Gly-Glu-Gly-Glu (SEQ ID NO: 5) DPA Gels After mixing of the cell suspension and 4% DPA solution by pipetting up and down, the protocol described above was modified by adding 10 µl 100 mg/ml calcium chloride solution upon which gelation occurred. Final concentrations are 2% in DPA and 100,000 cells. Control gels without cells were prepared by using pure media and additional cell only and cells with calcium chloride controls were prepared as standard 2D culture. After 7 days of culture, the gels were assayed with Live/Dead assay for cell viability and Invitrogen CyQuant GR assay for cell proliferation (Invitrogen, Carlsbad, Calif.). The Live/Dead was performed as described in the provided protocol but at half the ethidium bromide concentration to reduce non-specific fluorescence due to dye absorption. Cell controls showed predominantly live cells with a few dead cells. The cells in the gels contained a lot of viable cells (FIG. 410). No dead cells could be observed in the gels. Therefore, the viability of these cells in the gels is very high (>95%).

Figure 9A:
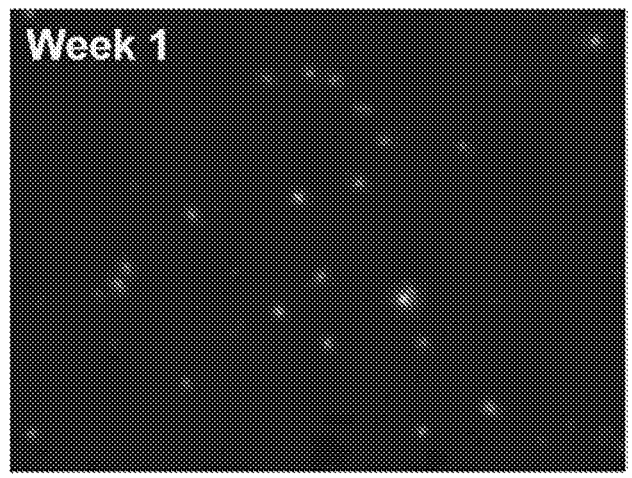
FIG. 9A. Cell viability of hUTCs after one week in Gly-Phe-Gly-Phe-Gly-Phe-Gly-Gln-Gln-Ser (SEQ ID NO: 8) DPA gels.
Figure 9B:
FIG. 9B. Cell viability of hUTCs after two weeks in Gly-Phe-Gly-Phe-Gly-Phe-Gly-Gln-Gln-Ser (SEQ ID NO: 8) DPA gels.
Figure 9C:
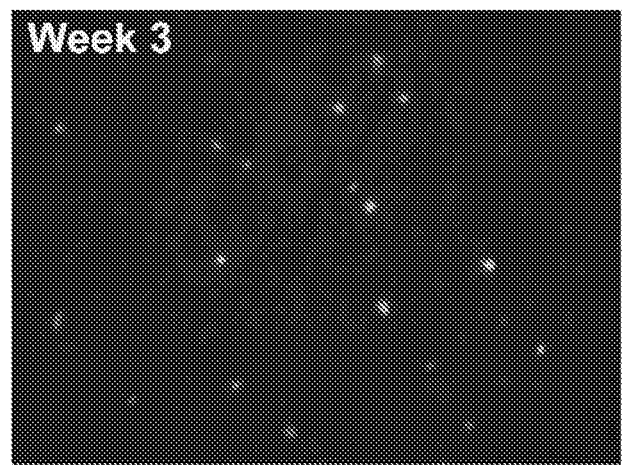
FIG. 9C. Cell viability of hUTCs after three weeks in Gly-Phe-Gly-Phe-Gly-Phe-Gly-Gln-Gln-Ser (SEQ ID NO: 8) DPA gels.
Figure 10:
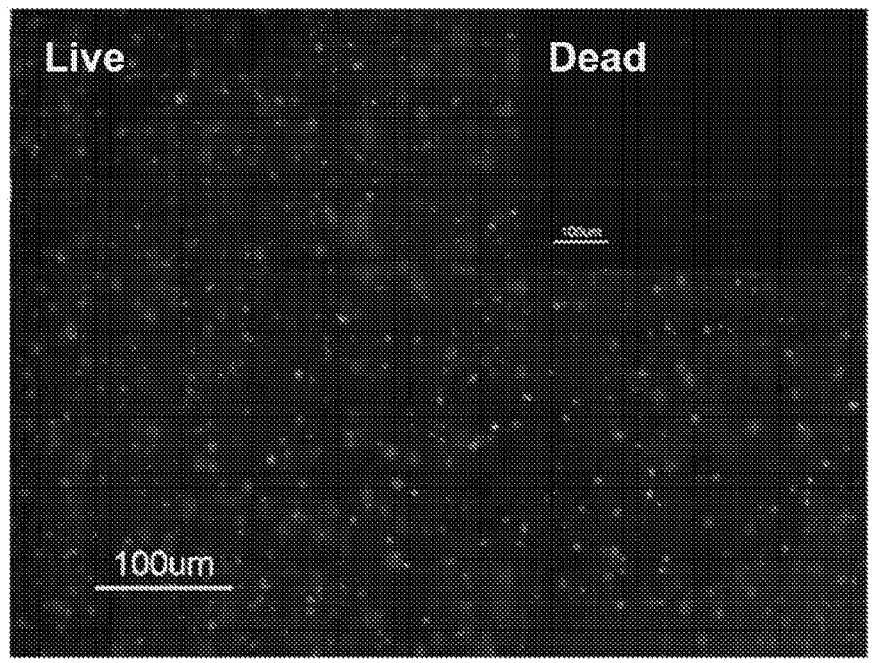
FIG. 10. Cell viability of hUTC cells in Gly-Phe-Gly-Phe-Gly-Phe-GlyGlu-Gly-Glu (SEQ ID NO: 5) DPA gels after 3 weeks of culture. Insert shows 'dead' image, main picture the live cells.

Cell Experiments with Gly-Phe-Gly-Phe-Gly-Phe-Gly-Gln-Gln-Ser (SEQ ID NO: 8) DPA Gels In a second experiment, 100,000 hUTC cells were encapsulated in 2 wt % Gly-Phe-Gly-Phe-Gly-Phe-Gly-Gln-Gln-Ser (SEQ ID NO: 8) DPA gels. The cells were cultured for 3 weeks and cells were assessed after 1, 2 and 3 weeks with Live/Dead. At all time points, very limited numbers of dead cells were detected, showing that viability remains good over the whole time period (FIG. 9A, FIG. 9B, and FIG. 9C).

Figure 11:
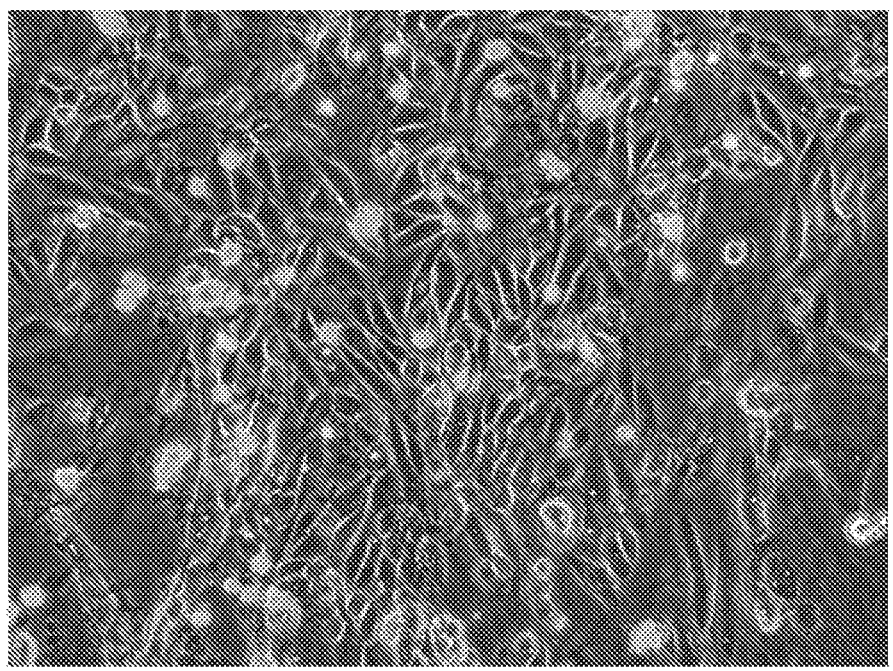
FIG. 11. Cell viability of hKDC cells in Gly-Phe-Gly-Phe-Gly-Phe-Gly-Gln-Gln-Ser (SEQ ID NO: 8) DPA gels after 3 weeks of culture.

Cell Viability of Human Kidney Derived (hKDCs) Cells in Gly-Phe-Gly-Phe-Gly-Phe-Gly-Gln-Gln-Ser (SEQ ID NO: 8) DPA Gels The viability and proliferation of cells in the gels was evaluated by encapsulating human kidney derived cells (hKDCs) in the gels. hKDC were isolated as described in US Patent Publication Number 2008/0112939. Cells were thawed from storage and cultured for four days in renal epithelial growth media (REGM) media. After four days, the cells were trypsinized and counted by the Guava ViaCount (Millipore, Billerica, Mass.) methodology. Cells were re-suspended in REGM media at a density of 1,000,000 cells/ml. Encapsulation of the cells in the gels was achieved by adding 100 µl cell suspension to 100 µl of a 4 wt % DPA solution in ultrapure in a 24 well plate, resulting in a final DPA concentration of 2%. The gels were incubated for 1 h at 37° C., 5% $CO_2$ after which 1000 µl media was added on top of the gel. Cells were incubated at 37° C., 5% $CO_2$. Every 3-4 days of culture, 500 µl media was replaced. The cells were cultured for 3 weeks and cells were assessed after 1, 2 and 3 weeks with Live/Dead. At all time points, very limited numbers of dead cells were detected, showing that viability remains good over the whole time period (FIG. 11).

Figure 12:
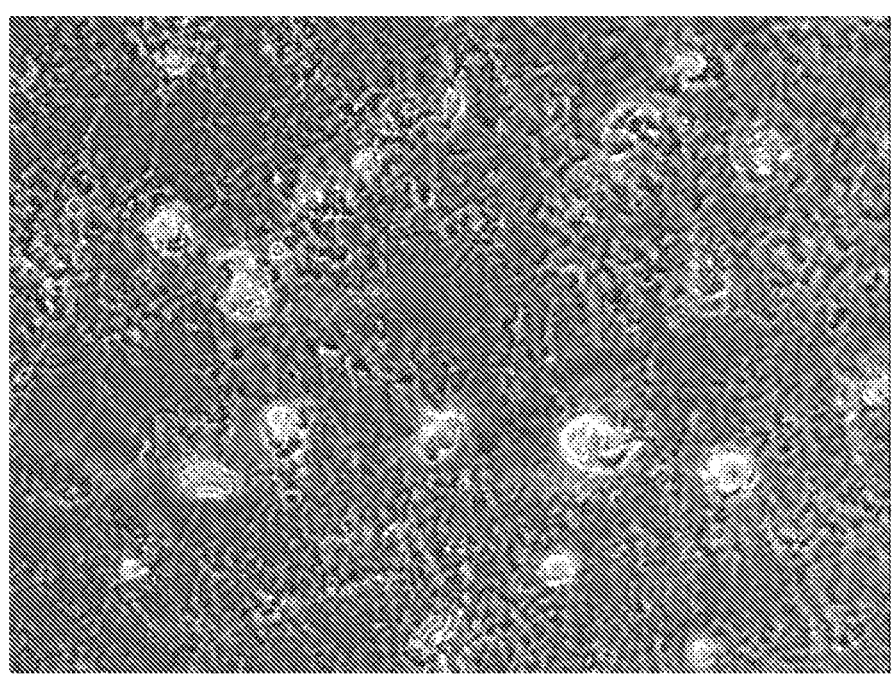
FIG. 12. Cell viability of IMAC cells in Gly-Phe-Gly-Phe-Gly-Phe-Gly-Ser (SEQ ID NO: 36) DPA gels after 3 weeks of culture.

Cell Viability of Internal Mammaray Artery (IMACs) Cells in Gly-Phe-Gly-Phe-Gly-Phe-Gly-Gln-Gln-Ser (SEQ ID NO: 8) DPA Gels The viability and proliferation of cells in the gels was evaluated by encapsulating human internal mammary artery derived cells (IMACs) in the gels. IMACs were isolated as described in copending U.S. patent application Ser. No. 12/885,855. Cells were thawed from storage and cultured for four days in advanced DMEM/F12 media. After four days, the cells were trypsinized and counted by the Guava ViaCount (Millipore, Billerica, Mass.) methodology. Cells were re-suspended in advanced DMEM/F12 media at a density of 1,000,000 cells/ml. Encapsulation of the cells in the gels was achieved by adding 100 µl cell suspension to 100 µl of a 4 wt % DPA solution in ultrapure in a 24 well plate, resulting in a final DPA concentration of 2%. The gels were incubated for 1 h at 37° C., 5% $CO_2$ after which 1000 µl media was added on top of the gel. Cells were incubated at 37° C., 5% $CO_2$. Every 3-4 days of culture, 500 µl media was replaced. The cells were cultured for 3 weeks and cells were assessed after 1, 2 and 3 weeks with Live/Dead. At all time points, very limited numbers of dead cells were detected, showing that viability remains good over the whole time period. The IMAC cells appear to have high motility in these gels as evidenced by the channels that they create in the gels. Over the course of the three week experiment, the number of channels increases significantly suggesting that they keep moving through the gel (FIG. 12).

Biocompatibility Study

Figure 13A:
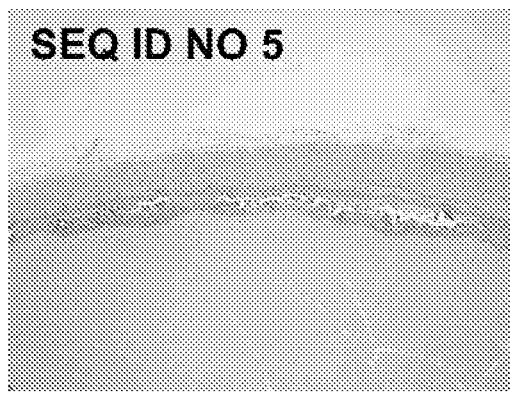
FIG. 13A. Histology of test articles (DPA prepared from SEQ ID NO: 5) at week 7.
Figure 13B:
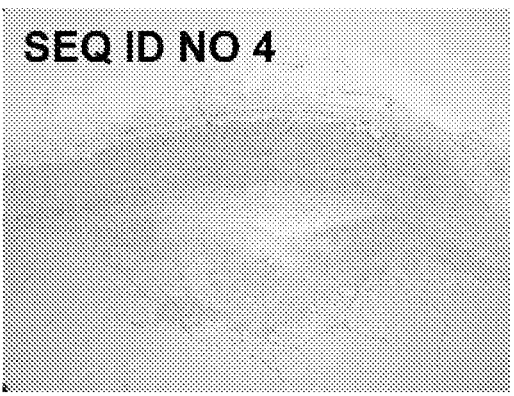
FIG. 13B. Histology of test articles (DPA prepared from SEQ ID NO: 4) at week 7.
Figure 13C:
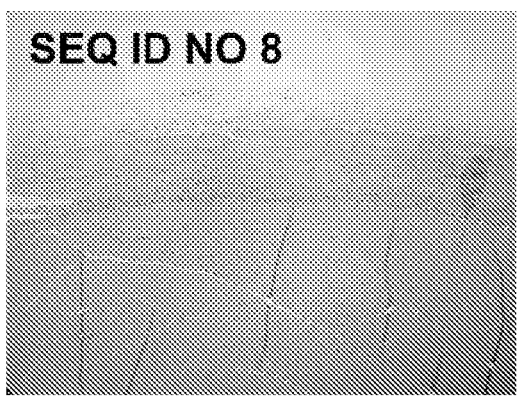
FIG. 13C. Histology of test articles (DPA prepared from SEQ ID NO: 8) at week 7.

A biocompatibility study was performed on Gly-Val-Ala-Val-Ala-Val-Ala-Glu-Gly-Glu (SEQ ID NO: 4), Gly-Phe-Gly-Phe-Gly-Phe-Gly-Glu-Gly-Glu (SEQ ID NO: 5) and Gly-Phe-Gly-Phe-Gly-Phe-Gly-Gln-Gln-Ser (SEQ ID NO: 8) DPAs. Lyophilized DPA powders were e-beam sterilized in 1.5 cc polypropylene cryovials at 15 KGy. Gels were pre-formed in 1 cc syringes by mixing a 4 wt % DPA solution in water for injection in a 1:1 ratio with DMEM followed by immediate aspiration into the syringe. In the case of the formulations with the Glu-Gly-Glu (SEQ ID NO: 27) sequence in the solubility enhancing region, 10 µl of a sterile 100 mg/cc calcium chloride solution was mixed in before aspiration into the syringe. An intra-gluteal muscle pocket was created in Sprague-Dawley rats after which 100 µl of gel was injected using a catheter fitted to the syringe. Subsequently, the pocket was closed with polyglactin 910 sutures sold under the tradename VICRYL (Ethicon, Somerville, N.J.). Tissue was harvested at 3, 7 and 28 days after implantation. Gross observations showed some fluid buildup at day 3, but this phenomenon was no longer observed at the other time points. After 28 days, the scaffolds are no longer detected. In the samples with the Glu-Gly-Glu (SEQ ID NO: 27) sequence in the solubility enhancing region, some necrosis of the underlying tissue layer was observed (FIG. 13A and FIG. 13B). The material with the Gln-Gln-Ser (SEQ ID NO: 28) sequence displayed a minimal immune response in histology (FIG. 13C). This demonstrates the benefit of gelation at physiological salt concentrations rather than supra-physiological salt concentrations.

Summary of Results and Conclusions

When the Gln-Gln-Ser (SEQ ID NO: 28) dicephalic peptide amphiphile was compared to the linear peptide amphiphile analogue and peptide analogue, the linear peptide amphiphile analogue required supraphysiological ion concentrations whereas the peptide analogue did not gel at all. Therefore, the dicephalic structure appears to be beneficial compared to other structural analogues of the same peptide. In addition, the observation of tissue necrosis for the test articles with supraphysiological salt concentrations in the biocompatibility study and the absence of such necrosis for the dicephalic peptide amphiphile gels that form at physiological salt concentrations demonstrate the benefit of these systems. The use of polar, non-charged amino acids allows for dicephalic peptide amphiphile systems that form gels under such conditions. The use of pi-pi stacking interactions in the self-assembly inducing region led to gels with improved mechanical properties. The shear-thinning behavior of the gels and re-forming of the gels after shear-thinning is beneficial for ease of administration into the body. Finally, it was demonstrated that a variety of cell types at a variety of densities can be encapsulated and remain viable over the course of at least three weeks.

We claim:

1. A dicephalic peptide amphiphile comprising the formula:

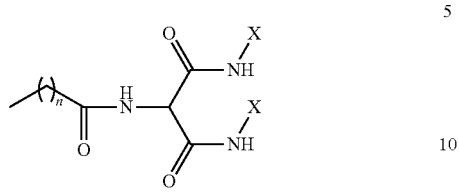

wherein n is equal to at least 6 and X is one of the peptide sequences selected from the group consisting of SEQ ID NO: 3, SEQ ID NO: 4, SEQ ID NO: 5, SEQ ID NO: 6, SEQ ID NO: 8, SEQ ID NO: 10, SEQ ID NO: 11, SEQ ID NO: 12, SEQ ID NO:13, SEQ ID NO: 14, SEQ ID NO: 15, SEQ ID NO: 16 and SEQ ID NO: 17.

2. The dicephalic peptide amphiphile of claim 1 wherein n is in the range of 6 to about 22.

3. The dicephalic peptide amphiphile of claim 2 wherein n is in the range of about 12 to about 18.

4. A hydrogel comprising the dicephalic peptide amphiphile of claim 1.

* * * * *